(12) United States Patent
Hu et al.

(10) Patent No.: US 11,506,658 B2
(45) Date of Patent: Nov. 22, 2022

(54) SYSTEM FOR ANALYSIS OF BODY FLUIDS AND WOUND-ASSOCIATED BIOMOLECULES

(71) Applicant: Progenitec Inc., Arlington, TX (US)

(72) Inventors: Wenjing Hu, Arlington, TX (US); Hong Vu, Arlington, TX (US); Ashwin Nair, Arlington, TX (US); Liping Tang, Arlington, TX (US)

(73) Assignee: Progenitec, Inc., Arlington, TX (US)

( * ) Notice: Subject to any disclaimer, the term of this patent is extended or adjusted under 35 U.S.C. 154(b) by 494 days.

(21) Appl. No.: 16/393,521

(22) Filed: Apr. 24, 2019

(65) Prior Publication Data

US 2020/0340981 A1 Oct. 29, 2020

(51) Int. Cl.
| | | |
|---|---|---|
| *G01N 33/52* | (2006.01) | |
| *G01N 33/84* | (2006.01) | |
| *A61F 13/84* | (2006.01) | |
| *C12Q 1/44* | (2006.01) | |
| *A61F 13/00* | (2006.01) | |

(52) U.S. Cl.
CPC ........... *G01N 33/525* (2013.01); *A61F 13/84* (2013.01); *C12Q 1/44* (2013.01); *G01N 33/84* (2013.01); *A61F 2013/00089* (2013.01); *A61F 2013/8491* (2013.01)

(58) Field of Classification Search
CPC .... G01N 33/525; G01N 33/84; G01N 33/526; A61F 13/84; A61F 2013/00089; A61F 2013/8491; A61F 13/00051; C12Q 1/44
See application file for complete search history.

(56) References Cited

U.S. PATENT DOCUMENTS

| | | |
|---|---|---|
| 4,356,149 A | 10/1982 | Kitajima et al. |
| 5,181,905 A | 1/1993 | Flam |
| 8,153,394 B2 | 4/2012 | Booher |
| 8,425,996 B2 | 4/2013 | Gorski et al. |
| 9,829,471 B2 | 11/2017 | Hammond et al. |
| 2007/0003606 A1 | 1/2007 | Booher |
| 2008/0193967 A1 | 8/2008 | Bommarito et al. |
| 2010/0178203 A1 | 7/2010 | Kane et al. |
| 2010/0279339 A1* | 11/2010 | Booher ................. A61B 5/445 435/34 |
| 2013/0064772 A1 | 3/2013 | Swiss et al. |
| 2016/0082142 A1 | 3/2016 | Wood et al. |
| 2016/0262672 A1 | 9/2016 | Hammond et al. |

(Continued)

FOREIGN PATENT DOCUMENTS

| | | |
|---|---|---|
| CN | 101588836 A | 11/2009 |
| CN | 109152860 A | 1/2019 |

(Continued)

*Primary Examiner* — Dennis White
(74) *Attorney, Agent, or Firm* — Cesari & McKenna, LLP

(57) ABSTRACT

A system for analyzing a wound fluid. The system includes a transparent layer, a membrane layer, and an indicator layer that contains a colorimetric or fluorescent indicator reagent for detecting pH, a nitrite, an enzyme, a reactive oxygen species, a reactive nitrogen species, a nucleic acid, or a combination thereof. The membrane layer is impermeable to blood clots and cellular debris and is permeable to wound fluid. Also provided are methods for analyzing a wound fluid and for detecting biological fluid on biomedical instruments and waste materials using the system.

17 Claims, 3 Drawing Sheets

Specification includes a Sequence Listing.

(56) References Cited

U.S. PATENT DOCUMENTS

2017/0000407 A1    1/2017   Saxby et al.
2019/0290799 A1    9/2019   Arshi et al.

FOREIGN PATENT DOCUMENTS

| CN | 109310528 A | 2/2019 | |
|----|----|----|----|
| EA | 2014/90319 A1 | 5/2014 | |
| EP | 0864864 A1 | 9/1998 | |
| WO | WO-2008/091521 A2 | 7/2008 | |
| WO | WO-2010/085755 A1 | 7/2010 | |
| WO | WO-2013/013799 A1 | 1/2013 | |
| WO | WO-2014/138470 A1 | 9/2014 | |
| WO | WO-2017/173069 A1 | 10/2017 | |
| WO | WO-2017173069 A1 * | 10/2017 | ............. A61L 15/56 |
| WO | WO-2018/046270 A1 | 3/2018 | |

* cited by examiner

I II

SEQUENCE LISTING

```
<160> NUMBER OF SEQ ID NOS: 1

<210> SEQ ID NO 1
<211> LENGTH: 4
<212> TYPE: PRT
<213> ORGANISM: Artificial Sequence
<220> FEATURE:
<223> OTHER INFORMATION: labelled peptide substrate

<400> SEQUENCE: 1

Ala Ala Pro Val
1
```

SYSTEM FOR ANALYSIS OF BODY FLUIDS AND WOUND-ASSOCIATED BIOMOLECULES

BACKGROUND

Wound fluid, also known as wound exudate, contains many biomolecules that can be analyzed in order to monitor wound healing and to detect infection. Several devices and techniques for analyzing wound fluid are currently in use.

For example, a suction device is available that collects wound exudate from a wound dressing covering the wound bed. The collected exudate is then analyzed using various biomolecule assay kits. The analysis can take hours to complete. Further, such a device cannot determine the presence of different biomolecules at different locations on the wound.

In another example, devices exist that contain embedded diagnostic reagents. They are used as wound dressings to cover wounds while simultaneously identifying and measuring biomolecules in wound fluid in situ. Including a wound contact layer made of a material similar to that of a wound dressing, these devices provide a limited number, typically one, of measurements of a single wound at a single time point. Also, as these devices come in direct contact with the wound, they must be sterilized prior to use, thereby limiting the diagnostic reagents that can be used. Further, these devices must be in place for several days before any meaningful analysis of wound biomolecules can be accomplished.

Moreover, there are many commercially available testing strips in which a test sample is placed on a non-porous paper strip to analyze various parameters in the sample, e.g., pH, esterase activity, and nitrite levels. These testing strips can only generate one value per test for a single parameter of each sample, typically representing a cumulative or average value for that parameter. These testing strips cannot be placed directly on a wound to analyze wound fluid, as tissue debris and blood clots in a wound may bind to the testing strip surface and thus interfere with the accuracy of the test.

The need exists for a system that can simultaneously measure and map biomolecules located at different areas of a wound without the drawbacks discussed above.

SUMMARY

To meet the need set forth, supra, a system for analyzing a wound fluid is provided. The system includes a transparent layer, a membrane layer, and an indicator layer. The indicator layer contains a colorimetric or fluorescent indicator reagent for detecting pH, a nitrite, an enzyme, a reactive oxygen species, a reactive nitrogen species, or a nucleic acid. The membrane layer is impermeable to blood clots and cellular debris and is permeable to wound fluid. The transparent layer is clear such that a color change of the colorimetric or fluorescent indicator reagent can be readily visualized through it.

Also provided is a method for analyzing a wound fluid using the above-described system. The method requires the steps of (i) obtaining a wound dressing that is impregnated with a wound exudate, (ii) covering the wound dressing with a surface of the membrane layer, (iii) contacting the indicator layer with the other surface of the membrane layer, (iv) incubating the wound dressing with the system such that the wound exudate transfers through the membrane layer to the indicator layer and components of the wound exudate react with the colorimetric or fluorescent indicator reagent in the indicator layer, and (v) visualizing one or more color changes in the indicator layer through the transparent layer. The color changes in the indicator layer are present at locations corresponding to the location in the wound dressing of the components of the wound exudate that reacted with the colorimetric or fluorescent indicator reagent.

Further disclosed is a method for detecting biological fluid on biomedical instruments and waste materials, also employing the system described above. The method is carried out by covering a biomedical instrument or waste material that has been in contact with a biological fluid, e.g., sweat, saliva, urine, plasma, and stool, with a surface of the membrane layer, contacting the indicator layer with the other surface of the membrane layer, incubating the biomedical instrument or waste material with the system such that the biological fluid transfers through the membrane layer to the indicator layer and reacts with the colorimetric or fluorescent indicator reagent in the indicator layer, and visualizing one or more color change in the indicator layer through the transparent layer. Similar to the previously described method, the color changes in the indicator layer are present at locations that came into contact with a component of the biological fluid material that reacted with the colorimetric or fluorescent indicator reagent.

The details of one or more embodiments of the invention are set forth in the drawings and description below. Other features, objects, and advantages of the invention will be apparent from the description, from the drawings, and from the appended claims.

BRIEF DESCRIPTION OF THE DRAWINGS

The description below refers to the accompanying drawings, of which.

DETAILED DESCRIPTION

Figure 1A:
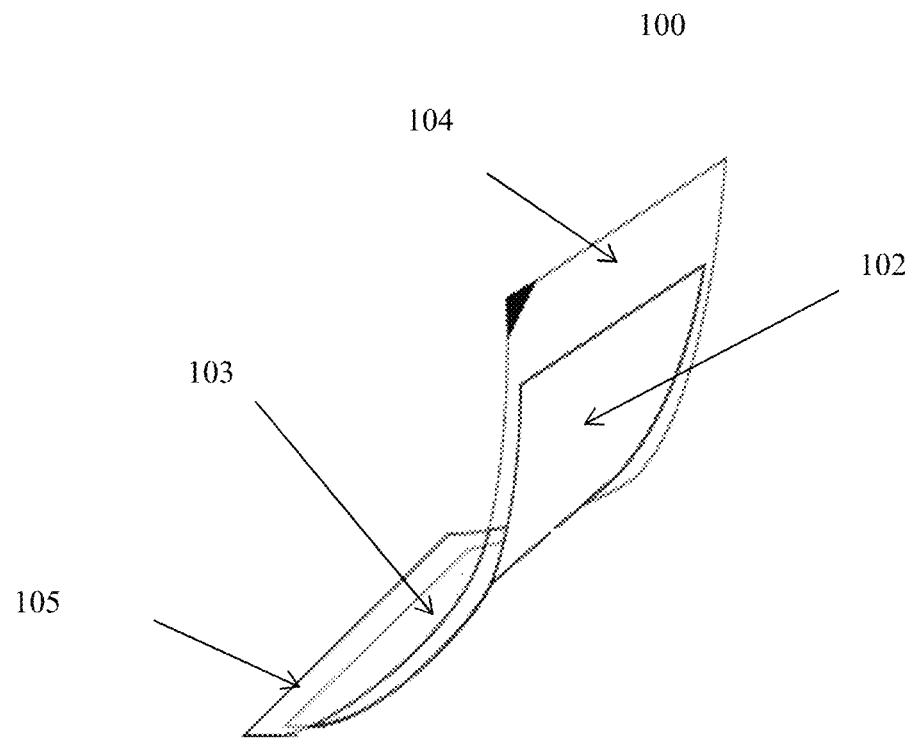
FIG. 1A is a diagram of a particular embodiment of a system of this invention for analyzing a wound fluid.

As mentioned above, a system for analyzing a wound fluid is provided that includes an indicator layer and a membrane layer. The indicator layer contains a colorimetric or fluorescent indicator reagent for detecting pH, a nitrite, an enzyme, a reactive oxygen species, a reactive nitrogen species, a nucleic acid, or combinations of these analytes. The colorimetric or fluorescent indicator reagent can be present in the indicator layer in an amount of 1 ng/cm$^2$ to 1 g/cm$^2$. In a particular example, the colorimetric or fluorescent indicator reagent is present in the indicator layer in an amount of 1 μg/cm$^2$ to 1 mg/cm$^2$.

For detection of pH, the indicator layer contains a pH sensitive indicator that can be, but is not limited to, nitrazine yellow (pH 6 to 7.2), bromocresol green (pH 3.8 to 5.4), chlorophenol red (pH 4.8 to 6.7), bromothymol blue (pH 6.0 to 7.6), phenol red (pH 6.8 to 8.4), thymol blue (pH 1.2 to 2.8 and pH 8.0 to 9.6), methyl red (pH 4.8 to 6.0), methyl orange (pH 3.1 to 4.4), methyl yellow (pH 2.9 to 4.0), propyl red (pH 4.8 to 6.6), Congo Red (pH 3.0 to 5.0), Alizarin Red S (pH 4.0 to 5.6), litmus, phenolphthalein, and other sulfonephthalein dyes, e.g., bromocresol purple (pH 5.2 to 6.8), cresol red (pH 0.2 to 1.8 and pH 7.2 to 8.8), and meta-cresol purple (pH 1.2 to 2.8 and pH 7.4 to 9.0).

Detection of nitrites is accomplished by including in the indicator layer a compound capable of reacting with nitrites, e.g., an aromatic primary amine that can be, but is not limited to, aniline; 4-chloroaniline; 4-bromoaniline; 2,4,6-tribromoaniline; 2,4,6-trichloroaniline; α-trifluoro-m-toluidine; ortho-toluidine; m- and p-aminophenol; ortho-tolidine; sulfanilamide, p-aminobenzoic acid; 1-amino-8-hydroxynaphthalene-3,6-disulphonic acid; aminoacetanilide; aminophenyl ether, p-arsanilic acid; and 4-amino-1-naphthalenecarbonitrile.

Exposure of nitrites to the indicator layer containing the above nitrite-reactive compounds results in the formation of diazonium salts not limited to 1-diazo-2-naphthol-4-sulfonate; 1-diazophenyl-3-carbonate; 4-diazo-3-hydroxy-1-naphthylsulfonate (DNSA); 4-diazo-3-hydroxy-7-nitro-1-naphthylsulfonate (NDNSA); 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. The diazonium salts react with tetrahydro-benzoquinoline to form pink-colored azo products.

As mentioned above, the system can also be used for detecting an enzyme such as a protease, an esterase, a lipase, and a peroxidase. For example, the system can be used for detecting elastase, a matrix metalloproteinase, catalase, myeloperoxidase (MPO), and cathepsin G.

For detection of an enzyme, the indicator layer can contain an enzyme substrate that produces a color or fluorescent signal in the presence of the active enzyme. In an example, the substrate is a protease substrate including a chromophore that emits a signal upon cleavage by a protease specific for the substrate. In a particular example, collagenase can be detected by labelled fragments of collagen I, II, III, IV, IX, which become fluorescent upon cleavage of the substrate by a collagenase. Similarly, a labelled elastase peptide substrate such as N-methoxysuccinyl-Ala-Ala-Pro-Val p-nitroanilide (SEQ ID NO: 1), and N-(methoxysuccinyl)-Ala-Ala-Pro-Val-7-amino-4-trifluormethylcoumarin is used for detecting elastase.

Esterase activity can be detected using a peptide substrate containing amino acid esters, e.g., 5-phenyl-3-hydroxypyrrolyl L-lactate, L-alanine-5-bromo-4-chloro-3-indoxyl ester, L-phenylalanine ethyl ester hydrochloride, 3-hydroxy-5-phenylpyrrole, and N-tosyl-L-alanine 3-indoxyl ester, in conjunction with a diazonium salt such as 1-diazo-2-naphthol-4-sulfonate; 1-diazophenyl-3-carbonate; DNSA; NDNSA; 4-diazo-3-hydroxy-1,7-naphthyldisulfonate; 2-methoxy-4-(N-morpholinyl) benzene diazonium chloride; 4-diazo-3-hydroxy-7-bromo-1-naphthylsulfonate; and 4-diazo-3-hydroxy-7-[1,oxopropyl]-1-naphthylsulfonate. In one example, the diazonium salts can be incorporated into the peptide.

In another example, the indicator layer contains particles of chitosan that release a dye upon hydrolysis by lysozyme.

In a further example an MPO substrate is included in the indicator layer, together with glucose oxidase and glucose, starch, and gamma-amylase.

Reactive oxygen species that can be detected by the system include, but are not limited to, superoxides, nitric oxide, tert-butyl hydroperoxide, hydroxyl radical, and hypochlorite. For detection of reactive oxygen species, the indicator layer contains, e.g., Amplex Red, 2-(2-pyridyl)-benzothiazoline, Bis-2,4-dinitrobenzenesulfonyl fluorescein, 2',7'-dichlorofluorescin diacetate, cyanine (Cy2, Cy3, Cy5)-based hydrocyanine or deuterocyanine, and luminol.

The system can be used to detect hypochlorous acid by including in the indicator layer HySOx or aminophenyl fluorescein and derivatives. Superoxides are detected by the system if the indicator layer contains Mito-SOX or 4-chloro-7-nitrobenzo-2-oxa-1,3-diazole. Alternatively, for detecting hypochlorite, the indicator layer includes one of naphthofluorescein disulfonate, pentafluorobenzene-sulfonyl fluorescein, Peroxifluor-1, Peroxycrimson-1, Peroxyresorufin-1, scopoletin, Spy-HP, and seminaphtho-phospha-fluorescein. In other examples, hydroperoxide is detected by MitoPY1 or diphenyl-1-pyrenylphosphine and hydroxyl radical by dihydrocalcein.

Reactive nitrogen species that can be detected by the system include, but are not limited to, nitric oxide, nitrogen dioxide radical, and nitrosonium cation. For detecting reactive nitrogen species, the indicator layer contains, e.g., o-phenylenediamine, 1,2-diaminoanthraquinone, 2,3-diamino naphthalene, 4,5-diaminofluorescein diacetate, 5,6-diaminofluorescein diacetate, diaminorhodamine-4M AM, 4,5-diaminorhodamine B, diaminocyanine, and rhodamine spirolactam.

For detection of nucleic acids, the indicator layer can contain crystal violet, ethidium bromide, propidium iodide, 7-aminoactinomycin D, 1,1'-(4,4,8,8-tetramethyl-4,8-diazaundecamethylene) bis[4-[(3-methylbenzo-1,3-oxazol-2-yl) methylidene]-1,4-dihydroquinolinium] tetraiodide (YOYO-1™), 1-1'-[1,3-propanediylbis [(dimethyliminio)-3,1-propanediyl]]bis[4-[(3-methyl-2(3H)-benzothiazolylidene) methyl]] tetraiodide (TOTO-1™), 4',6-diamidino-2-phenylindole, Hoechst 33258, 33342, 34580) acridine orange, or hydroxystilbamidine.

Moreover, the indicator layer can contain 3,3'-diaminobenzidine, 3,4 diaminobenzoic acid, dichlorophenolindophenol, N,N-dimethyl-p-phenylenediamine, o-dianisidine, 4-chloro-1-naphthol, o-phenylenediamine, N-(4-aminobutyl)-N-ethylisoluminol, 3-amino-9-ethylcarbazole, 4-aminophthalhydrazide, 5-aminosalicylic acid, 2,2'-azino-bis(3-ethylbenzothiazoline-6-sulfonic acid), indoxyl, indigo, Fast Blue RR, 4-chloro7-nitrobenzofurazan.

Furthermore, the indicator layer can contain an amino phenol, an aminophenol ether, a neutral dye, a charged dye, a reactive dye containing a sulfonyl ethyl hydrogen sulphate reactive group, or a dichlorotriazine-based reactive dye.

The charged dye can be remazol brilliant blue R, toluidine blue, reactive black 5, reactive violet 5, and reactive orange 16, or a hydrolytic or ammonolytic derivative thereof.

The dichlorotriazine-based reactive dyes can be reactive blue 4, reactive red 10, reactive blue 2, reactive red 120, reactive green 19 and reactive brown 10. The dichlorotriazine-based reactive dye can appear black.

The indicator layer can include nanoparticles or colloidal gold particles, which can be functionalized to be reactive to specific analytes. Nanoparticles or colloidal gold particles containing distinct colorimetric or fluorometric indicator reagents can be employed in the indicator layer to enable the system to sense multiple analytes.

As mentioned above, in addition to the indicator layer, the system includes a membrane layer. The membrane layer is impermeable to blood clots and cellular debris and is permeable to wound fluid. The membrane layer can be 5 µm to 1.0 mm thick and have a pore size of 5 nm to 50 µm. In certain systems, the membrane layer is 0.1 mm to 0.6 mm thick and has a pore size of 5 µm to 50 µm. In a particular system, the membrane layer is 0.2 mm to 0.3 mm thick and has a pore size of 20 µm to 30 µm.

The membrane layer is designed to transport biological fluids from a test item, e.g., a wound dressing, to the indicator layer, while at the same time, preventing blood clots and tissue debris in the wound dressing from directly contacting the indicator layer. The membrane layer can be formed of cellulose, nitrocellulose, methyl cellulose, hydroxypropyl cellulose, hydroxyethyl cellulose, hydroxypropyl methyl cellulose, ethyl hydroxyethyl cellulose, carboxymethyl cellulose, cellulose acetate, cellulose acetate butyrate, cellulose acetate propionate, cellulose nitrate nylon, nylon, viscose, cotton, rayon, wool, silk, (poly) hydroxyethyl methacrylate, (poly) hydroxypropyl methacrylate, (poly) glycerol methacrylate, copolymers of hydroxyethyl methacrylate, hydroxypropyl methacrylate, or glycerol methacrylate and methacrylic acid, aminoacrylate and amino methacrylate, poly 4-vinylpyridine, polyvinyl acetate, polyvinyl alcohol, copolymers of polyvinyl acetate and polyvinyl alcohol, hydroxyl modified copolymers of vinyl acetate and vinyl chloride, polyesters and polyurethanes containing at least 10% by weight polyethylene oxide, styrene, methacrylic acid/hydroxyethyl methacrylate copolymers, methyl methacrylate/methacrylic acid copolymers, ethyl methacrylate/styrene/methacrylic acid copolymers, ethyl methacrylate/methyl methacrylate/styrene/methacrylic acid copolymers, and polytetrafluoroethylene. In particular systems, the membrane layer is formed of cellulose, nitrocellulose, or nylon.

The system also includes a non-porous waterproof transparent layer that overlays the indicator layer. The transparent layer is clear such that a color change of the colorimetric or fluorescent indicator reagent can be readily visualized through the transparent layer. The transparent layer can be formed of a clear plastic, glass, or a polymer film. For example, the transparent layer can be polypropylene, polystyrene, polyvinyl chloride (PVC), polyvinyl alcohol, cellulose acetate, acrylic or poly(vinyl acetate) polymers, polyethylene-terephthalate, polyurethane, polyacrylate, polycarbonate, ethylene-vinyl acetate, styrene-acrylic acid copolymer, styrene-methacrylic acid copolymer, or combinations of these materials.

In one system, the indicator layer is integral with the transparent layer. In another system, the indicator layer is integral with the membrane layer.

The indicator layer can be formed integral with the transparent layer or with the membrane layer by means of an adhesive to retain one or more indicator reagents to the transparent layer or to the membrane layer. Adhesives that can be used include, but are not limited to, acrylic, epoxies, polyvinyl acetate, polyurethane, dextrin, casein, latex, peroxide, isocyanate, urea-formaldehyde resin, acrylonitrile, cellulose nitrate, neoprene base, polysulfide, PVC, rubber-based glue, silicon-based glue, and albumin glue.

In a particular system, the adhesive is an acrylic glue having a neutral pH. In another particular system, the glue is polyvinyl acetate.

In an alternative system, a base layer is also included, together with the transparent layer, the indicator layer, and the membrane layer. The base layer is non-porous and waterproof to prevent any liquid, e.g., wound exudate, from leaking out of the system during use. The base layer is white or light in color, to facilitate viewing color changes in the indicator layer.

The base layer, which can be rigid or flexible, is formed of, e.g., a plastic, a ceramic, aluminum, nylon, PVC, poly (vinylidene fluoride), poly(vinylidene chloride), phenoxy resins, butadiene/styrene copolymers, butadiene/methylstyrene copolymers, poly(meth)acrylates, butadiene/acrylonitrile copolymers, ethylene/propylene copolymers, polybutadiene, polyisoprene, poly(oxy-2,6-dimethyl-1,4-phenylene), poly(oxycarbonyloxy-1,4-1,4-phenyleneisopropylidene-1, 4-phenylene), acrylonitrile Styrene copolymers, acrylonitrile/methyl acrylate/butadiene copolymers, acrylonitrile/styrene-butadiene copolymers, poly-1-vinylnaphthalene, polyvinyl phenyl ketone, poly-p xylylenedodecanedioate, poly-tetramethylene octenediamide, poly-(tetramethylene terephthalene), poly-(trimethylene 3,3'-dibenzoate), poly-(terephthallic anhydride), poly-(4-methyl-diamine), polyvinylene carbonate, polyvinyl laurate, poly(isopropenyl acetate), poly(allylbenzene), poly(vinyl butyl ether), polyvinyl formate, polyvinyl phenyl ether, polynorbornene, polycarbonate, hydrophobic polyesters and polyurethanes, and mixtures of these materials. In an exemplary system, the base layer is PVC.

In a particular example of a system having three layers, i.e., the transparent layer, the indicator layer, and the membrane layer, all of the layers are physically joined along an edge. In a specific example, the transparent layer and the membrane layer are joined along an edge, and the indicator layer does not extend to that edge.

In another example, the system has four layers, i.e., the transparent layer, the indicator layer, the membrane layer, and the base layer, all of which are physically joined along an edge. In a specific arrangement, the transparent layer, the membrane layer, and the base layer are joined along an edge, and the indicator layer does not extend to that edge.

The system can be further described with reference to FIG. 1A. This figure shows system 100 for analyzing a wound fluid. System 100 includes membrane layer 102, transparent layer 104, and indicator layer 103 between membrane layer 102 and transparent layer 104. In the particular arrangement shown, transparent layer 104 and membrane layer 102 are connected along edge 105. In another arrangement, all of the layers, i.e., transparent layer 104, membrane layer 102, and indicator layer 103 extend to and are connected along edge 105.

Figure 1B:
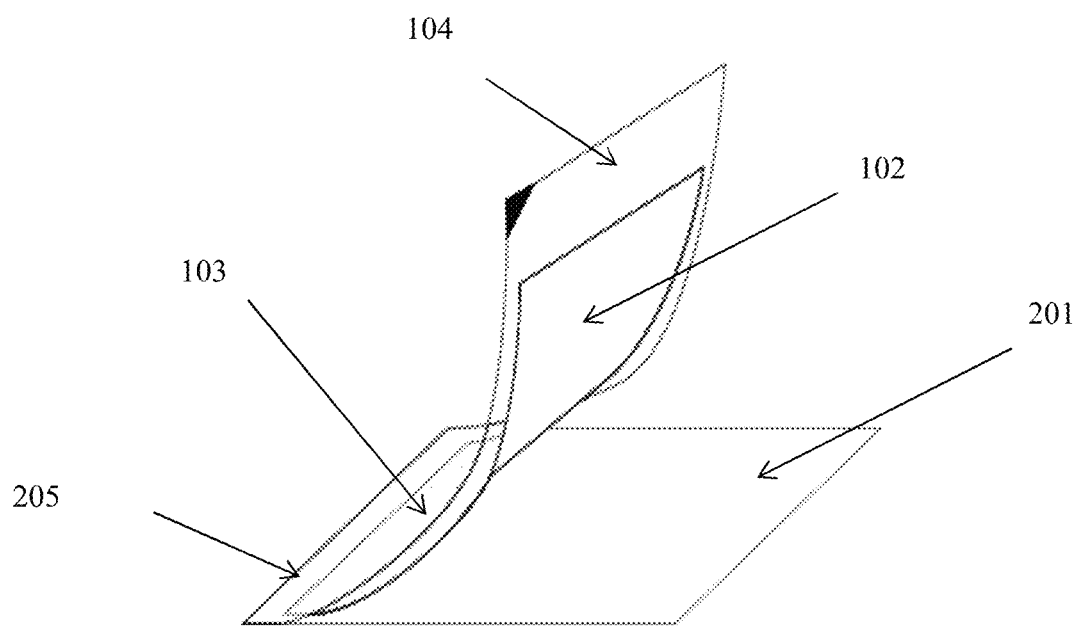
FIG. 1B is a diagram of an alternative embodiment of this invention

Also within the scope of the invention is system 200 shown in FIG. 1B. This system includes base layer 201, membrane layer 102, transparent layer 104, and indicator layer 103 between membrane layer 102 and transparent layer 104. In the depicted arrangement, base layer 201, transparent layer 104, and membrane layer 102 are connected along edge 205. In another arrangement, base layer 201, transparent layer 104, membrane layer 102, and indicator layer 103 extend to and are connected along edge 205.

Turning to indicator layer 103, this layer, as mentioned above, contains an indicator reagent for colorimetric or fluorescent detection of pH, nitrites, proteases (e.g., an esterase), reactive oxygen species, and reactive nitrogen species. In system 100 and system 200, indicator layer 103 can be a separable, distinct layer, it can be integrated with transparent layer 104, or it can be integrated with membrane layer 102. For example, the indicator reagent can be attached with an adhesive to transparent layer 104 to form indicator layer 103. In another example, the indicator reagent is attached to membrane layer 102 with an adhesive. Alternatively, the indicator reagent can be chemically crosslinked to either transparent layer 104 or to membrane layer 102. In a further alternative, the indicator reagent is impregnated into membrane layer 102 and held in place by physical entrapment and electrostatic forces.

Transparent layer 104 is a protective layer that prevents the indicator reagent in indicator layer 103 from being washed out. It is clear to enable visualization of color changes of the dye in indicator layer 103. Transparent layer 104 is also waterproof and non-porous such that wound fluid will not penetrate it, thereby providing safety for users of system 100 and system 200. Transparent layer 104 can be formed of clear materials as listed above.

Turning to base layer 201, it is designed to provide mechanical support for system 200. Base layer 201, like transparent layer 104, is waterproof and non-porous to prevent leakage of and contamination by biological fluids under analysis. As mentioned above, base layer 201 is white or light in color to enhance visualization of color changes in indicator layer 103. Materials that can be used to form base layer 201 are set forth, supra.

The system described in detail above can be used in a method for analyzing a wound fluid. The method is carried out by obtaining a system that includes an indicator layer and a membrane layer, obtaining a wound dressing that is impregnated with a wound exudate, covering the wound dressing with the membrane layer, contacting the indicator layer with the membrane layer, incubating the wound dressing with the system such that the wound exudate transfers through the membrane layer to the indicator layer, where components of the wound exudate, e.g., biomolecules, react with the colorimetric or fluorescent indicator reagent, and visualizing a color change in the indicator layer through the transparent layer.

The color change in the indicator layer is present at a location corresponding to the original location in the wound dressing of the wound exudate component that reacted with the indicator reagent. The color change reflects the quantity and location of these components in different areas of the wound. As such, a map is created showing the particular location in the wound of a certain attribute, e.g., alkaline pH, or biomolecule, e.g., an esterase. The map thus created can be preserved, for example, by taking a photograph or by digital scanning.

A particular method can be carried out to analyze a dry wound dressing. In this method, the steps discussed in the preceding paragraph are carried out with the addition of a step in which the wound dressing is hydrated with a salt solution.

The salt solution is a high molar (0.5-6 M) solution having a high pH (pH 7-11). The salt solution can be, but is not limited to, 1-6 M NaCl, 0.5-3.5 M KCl, 3 mM-3 M KI, 1.7-17 M $KH_2PO_4$, 9 mM-9M $K_2HPO_3$, 0.3-3.5 M $Na_2CO_3$, or 0.5-4 M tris(hydroxy methyl) aminomethane.

Hydration of the wound dressing can be carried out by applying the salt solution to the wound dressing, e.g., by spraying, prior to covering it with the membrane layer. Alternatively, the salt solution can be applied to the membrane layer prior to covering the wound dressing.

In a particular method, the system employed includes the base layer, in addition to the transparent layer, the membrane layer, and the indicator layer. All of the layers can be joined along a single edge.

The above-described system can also be used in a method for detecting biological fluid on biomedical instruments and waste materials. The method is carried out by obtaining a system that includes an indicator layer and a membrane layer, obtaining a biomedical instrument or waste material that has been in contact with a biological fluid, covering the biomedical instrument or waste material with the membrane layer, contacting the indicator layer with the membrane layer, incubating the biomedical instrument or waste material with the system such that the biological fluid transfers through the membrane layer to the indicator layer and reacts with the colorimetric or fluorescent indicator reagent, and visualizing a color change in the indicator layer.

The color change in the indicator layer is present at a location corresponding to a location that came into contact with a component of the biological fluid present on the biomedical instrument or waste material and reacted with the colorimetric or fluorescent indicator reagent. The detection result can be preserved by taking a photograph or by digital scanning.

Without further elaboration, it is believed that one skilled in the art can, based on the disclosure herein, utilize the present disclosure to its fullest extent. The following specific examples are, therefore, to be construed as merely descriptive, and not limitative of the remainder of the disclosure in any way whatsoever.

EXAMPLES

Example 1: Analysis of Uninfected Porcine Skin Wounds

The efficacy of the system was tested on cotton gauze dressings freshly recovered from porcine skin wounds.

Wounds undergoing active healing and acute inflammatory responses have an acidic environment, which was detected by the pH detection system. On the other hand, chronic and non-healing wounds display an alkaline environment, which was also detected by the pH detection system.

Excisional wounds were made in animals by removing full thickness skin tissue down through the fascia to the surface of the underlying muscle. Wounds were covered with cotton gauze dressings, which were changed on days 1, 3, 5, 7, 14, 21, and 28 days after wounding. The freshly removed gauzes were tested for wound pH and esterase activities using two examples of the system as described above.

Both particular examples used had a base layer, a membrane layer, an indicator layer, and a transparent layer. Both the base layer and the transparent layer were formed of polyethylene terephthalate. The membrane layer was formed of cellulose having a thickness of 0.25 mm and a pore size of 20 to 35 µm.

For detection of pH, the system included 5 mg of yellow nitrazine as the indicator layer, coated onto a 10×10 $cm^2$ cellulose membrane layer.

For detecting esterase activity, the system employed 1.4 mM N-tosyl-L-alanine 3-indoxyl ester and 10 mM 1-Diazo-2-naphthol-4-sulfonic acid in ethanol as the indicator layer coated onto a 10×10 $cm^2$ cellulose membrane layer.

Figure 2:
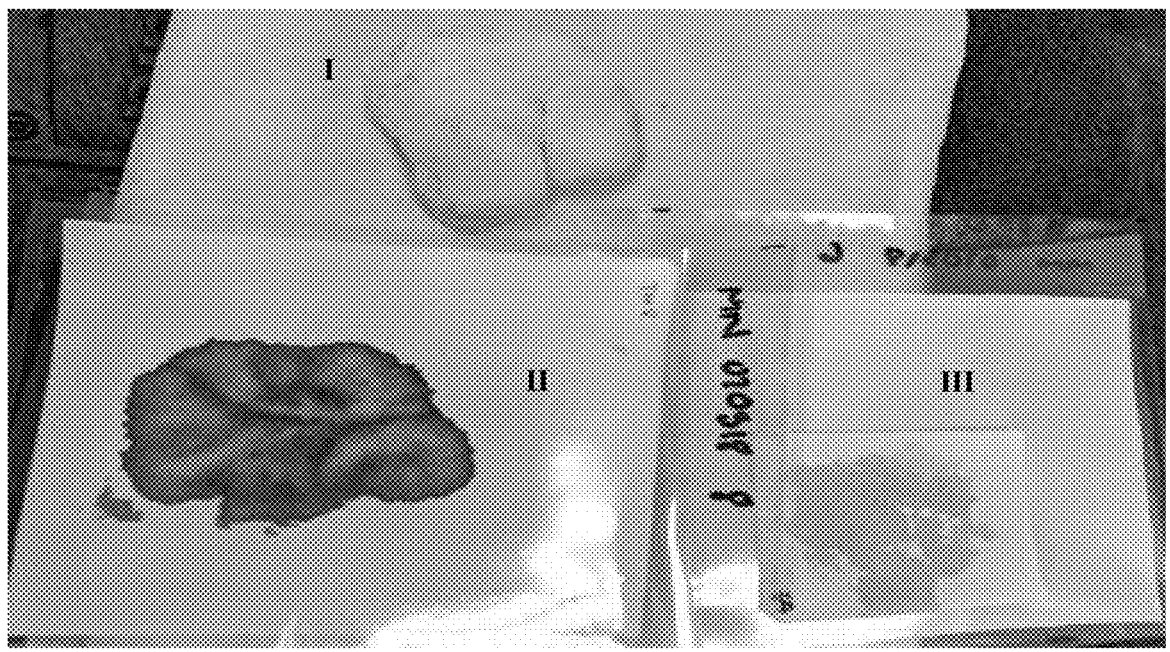
FIG. 2 is a photograph showing detection of active inflammation in the absence of infection in a pig wound after transfer of wound fluid from wound gauze (I) to a pH indicator layer (II) and to an esterase activity indicator layer (III)

Two days after wounding, the gauze was recovered and placed in a detection system for up to 10 s against the membrane layer described above coated with yellow nitrazine as the pH detection reagent. The wound exudate on the gauze had an acidic pH of ~6, indicative of an active inflammatory response typically seen in a healing wound. See FIG. 2, panel II.

The same gauze was then placed onto the esterase detection system for up to 10 s to determine whether or not infection was present. The result showed no color change in the membrane layer containing the esterase detection reagent, indicating the absence of infection. See FIG. 2, panel III.

Twenty-one days after wounding, a gauze that had been in place for 7 days was removed from the wound and placed onto the pH detection system described above for up to 10 s. The pH detection system showed that wound fluid in the gauze was alkaline (pH~8), indicating low inflammatory activity. The same gauze tested in the esterase detection system showed low esterase activity, consistent with the absence of infection.

Example 2: Analysis of Infected Porcine Skin Wounds

Tissue fluid from an infected wound contains a high level of esterase enzyme activity, which was detected by the esterase detection system. By contrast, fluid from a non-infected wound contains little or no esterase activity, which was shown by an absence of reactivity with the esterase detection system.

Figure 3:
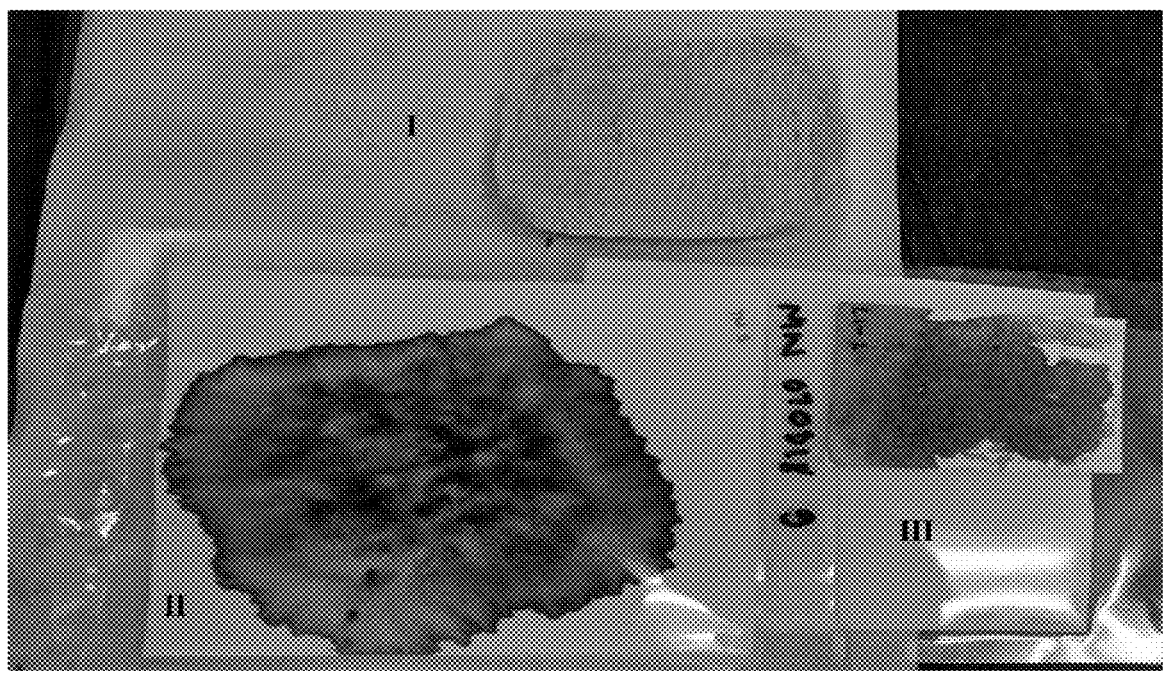
FIG. 3 is a photograph showing detection of active inflammation and infection in a pig wound after transfer of wound fluid from wound gauze (I) to a pH indicator layer (II) and to an esterase activity indicator layer (III).

Full thickness skin wounds were made in pigs as described in Example 1. These wounds were treated with 2000 colony-forming units of *Pseudomonas aeruginosa* (American Type Culture Collection 27853) prior to placing the cotton gauze dressings. As in Example 1, the gauze was changed on days 1, 3, 5, 7, 14, 21, and 28. Two days after wounding and infection with *P. aeruginosa*, the gauze was removed from the infected wound and inserted into the systems described in the preceding paragraph. The pH of the gauze was acidic, having a pH~6. This indicated that an inflammatory response was ongoing. See FIG. 3, panel I. Again, the same gauze was placed on an esterase detection system that determines the presence or absence of infection. The esterase detection reagent reacted strongly with wound exudate from the gauze, showing high esterase activity associated with the infection. See FIG. 3, panel III.

Fourteen days after wounding and infection, a gauze that had been in place for 7 days was removed from the wound and placed for up to 10 s onto the pH detection system described above. The pH detection system showed that wound fluid in the gauze was alkaline (pH~8), indicating low inflammatory activity. The same gauze tested in the esterase detection system showed low esterase activity, consistent with the absence of infection.

Example 3: Analysis of a Human Healing Chronic Skin Wound

Figure 4:
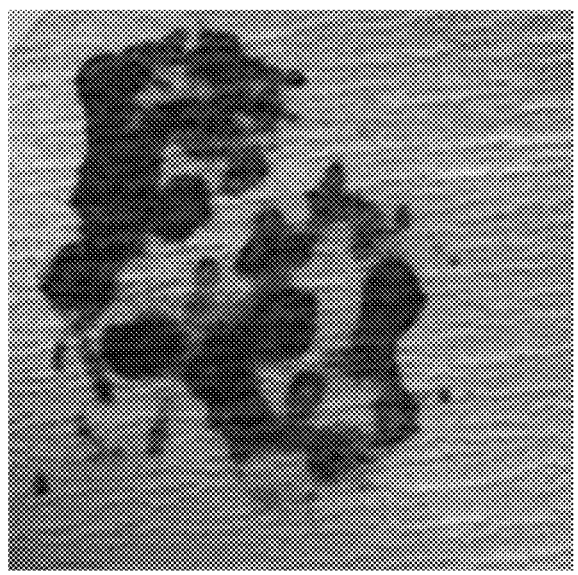
FIG. 4 shows photographic results of the detection of distinct healing and non-healing wound areas and absence of infection in a human chronic skin wound after transfer of wound fluid from wound gauze to a pH indicator layer (I) and to an esterase activity indicator layer (II).
Figure 4:

A chronic skin wound showing signs of healing in a human patient was analyzed using the system set forth above. Wound gauze placed in the pH sensing system showed yellow areas of acidic pH, which appear as light areas in FIG. 4, panel I, interspersed with dark blue alkaline patches, which appear as dark areas in the same figure. See FIG. 4, panel I. The acidic patches corresponded to areas showing normal inflammatory and healing activities, while the alkaline patches corresponded to areas in which healing had stopped or slowed down.

The same chronic wound that had begun to heal was tested for infection by placing the wound dressing onto the esterase detection system. The results showed no color change, indicating that the chronic wound was not infected. See FIG. 4, panel II.

Example 4: Analysis of a Non-Healing Human Skin Wound

An analysis was also performed on a wound dressing removed from a non-healing human skin wound. The dressing was removed from the wound and placed onto the above pH detection system. The results showed homogeneous alkalinity across the dressing, correlating with the absence of inflammation associated with the wound healing process.

The same dressing was tested for esterase activity in the esterase detection system. The analysis showed distinct regions of purple coloration resulting from esterase activity in the wound, indicating areas of infection. The wound infection was confirmed by standard laboratory testing.

Example 5: Blocking Transfer of Blood Through the System

A membrane layer of the system was tested for its ability to prevent blood and cellular debris from penetrating through it to the indicator layer. The membrane layer was coated on one side with a pH indicator layer as described above in Example 1. A bloody wound dressing was applied to the surface of the membrane opposite to the surface coated with the indicator layer. The indicator layer turned dark blue within 10 s after application of the wound dressing to the membrane surface and showed no red staining. This result showed that wound exudate could be transported from the dressing through the membrane layer to the indicator layer while blood cells in the dressing were not transferred. By contrast, the surface of the membrane layer that was in contact with the wound dressing was stained red by blood cells from the dressing.

Example 6: Analysis of Dried Wound Dressing after Hydration

As mentioned above, the system can be used on dry wound dressings by hydrating the wound dressing with a hydration solution. The hydration solution dissolves dried wound fluid components and allows them to be transferred to the system.

Two hydration solutions, namely, 6M NaCl pH 10.6 and 4M KCl pH 10.6, were tested by spotting 200 µL samples of each solution onto the membrane layer of a pH detection system as described in Example 1. Neither sample was detected by the system, as no color change was seen in the indicator layer.

Gauze that was freshly removed from a human skin wound was placed on the membrane layer of the pH detection system, resulting in no color change. The same gauze was removed from the system, hydrated by spraying it with 4 M KCl, pH 10.6, and replaced against the membrane layer. A light blue color appeared in the indicator layer, signifying an alkaline pH.

A gauze that was freshly removed from a second dry human skin wound and placed on the membrane layer of the pH detection system showed several widely separated blue spots on the indicator layer. The gauze was removed from the system, sprayed with 6 M NaCl pH 10.6, and replaced into the system. The hydrated gauze showed widespread blue color, indicative of an alkaline environment in the wound.

Example 7: Detection of pH in Pig Dry Wound Gauze

Gauze was removed from a pig skin wound 17 days after the wound was made and allowed to air dry. The dry gauze placed into a pH detection system did not produce any color change in the pH indicator layer. After hydrating the gauze with a solution of 4 M KCl pH 10.6, the gauze was placed back into the system. The hydrated gauze induced a light blue color in the indicator layer, consistent with an alkaline wound fluid.

In a second test, a gauze was removed from a 17-day pig wound and dried as described in the preceding paragraph. Testing the dried gauze in a pH detection system failed to show any color change in the pH indicator layer. The dried gauze was hydrated by spraying it with a 4 M KCL solution pH 10.6. Upon replacing the now hydrated gauze into the system, a pattern of light blue/yellow colors appeared in the indicator layer of the system, indicating a mixed acidic/alkaline wound fluid with areas of active inflammation in the wound.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

2. The system of claim 1, wherein the membrane layer is 5 μm to 1.0 mm thick and has a pore size of 5 nm to 50 μm.

3. The system of claim 2, wherein the membrane layer is 0.1 mm to 0.6 mm thick and has a pore size of 5 μm to 50 μm.

4. The system of claim 1, wherein the colorimetric or fluorescent indicator reagent is present in the indicator layer in an amount of 1 μg/cm$^2$ to 1 mg/cm$^2$.

5. The system of claim 1, wherein the membrane layer is formed of one or more of cellulose, nitrocellulose, methyl cellulose, hydroxypropyl cellulose, hydroxyethyl cellulose, hydroxypropyl methylcellulose, ethyl hydroxyethyl cellulose, carboxymethyl cellulose, cellulose acetate, cellulose acetate butyrate, cellulose acetate propionate, cellulose nitrate nylon, nylon, viscose, cotton, rayon, wool, silk, (poly) hydroxyethyl methacrylate, (poly) hydroxypropyl methacrylate, (poly) glycerol methacrylate, copolymers of hydroxyethyl methacrylate, hydroxypropyl methacrylate, or glycerol methacrylate and methacrylic acid, aminoacrylate and amino methacrylate, (poly) vinylpyridine, polyvinyl acetate, polyvinyl alcohol, copolymers of poly 4-vinylacetate and polyvinyl alcohol, hydroxyl modified copolymers of vinyl acetate and vinyl chloride, polyesters and polyurethanes containing at least 10% by weight polyethylene oxide, styrene, methacrylic acid/hydroxyethyl methacrylate copolymers, methyl methacrylate/methacrylic acid copolymers, ethyl methacrylate/styrene/methacrylic acid copolymers, ethyl methacrylate/methyl methacrylate/styrene/methacrylic acid copolymers, or polytetrafluoroethylene.

What is claimed is:

1. A system for analyzing a wound fluid, the system comprising a non-porous waterproof base layer, a transparent layer, an indicator layer, and a membrane layer, the indicator layer containing a colorimetric or fluorescent indicator reagent for detecting one or more of pH, a nitrite, a protease, an esterase, a reactive oxygen species, a reactive nitrogen species, and a nucleic acid, wherein the membrane layer is impermeable to blood clots and cellular debris and is permeable to wound fluid, the indicator layer is located in between the transparent layer and the membrane layer, the colorimetric or fluorescent indicator reagent is present throughout the indicator layer in an amount of 1 ng/cm$^2$ to 1 g/cm$^2$, the transparent layer, being non-porous, is clear such that a color change of the colorimetric or fluorescent indicator reagent can be visualized through the transparent layer, and the base layer, the membrane layer, and the transparent layer are joined together along a single edge, the base layer for preventing liquid from leaking out of the system during use.

6. The system of claim 5, wherein the membrane layer is formed of cellulose, nitrocellulose, or nylon.

7. The system of claim 6, wherein the membrane layer is 5 μm to 1.0 mm thick and has a pore size of 5 nm to 50 μm.

8. The system of claim 7, wherein the colorimetric or fluorescent indicator reagent for detecting pH is selected from the group consisting of nitrazine yellow, bromocresol green, chlorophenol red, bromothymol blue, phenol red, thymol blue, methyl red, methyl orange, methyl yellow, propyl red, litmus, phenolphthalein, and a sulfonephthalein indicator.

9. A method for analyzing a wound fluid, the method comprising:
obtaining a system of claim 1 that includes a transparent layer, an indicator layer, and a membrane layer having a first surface and a second surface opposed to the first surface, the indicator layer being located between the transparent layer and the second surface,
obtaining a wound dressing that is impregnated with a wound exudate, covering the wound dressing with the membrane layer such that the first surface of the membrane layer is in contact with the wound dressing, contacting the indicator layer with the second surface of the membrane layer, incubating the wound dressing with the system such that the wound exudate transfers through the membrane layer to the indicator layer and components of the wound exudate react with the colorimetric or fluorescent indicator reagent, and visualizing one or more color changes in the indicator layer through the transparent layer, wherein the one or more color changes in the indicator layer are each present at a location corresponding to the location in the wound dressing of the components of the wound exudate that reacted with the colorimetric or fluorescent indicator reagent.

10. The method of claim 9, further comprising hydrating the wound dressing with a salt solution having a pH of 5-11 and a concentration of 1-6 M.

11. The method of claim 10, wherein the salt solution contains NaCl, KCl, KI, $KH_2PO_4$, $K_2HPO_4$, or tris(hydroxymethyl)aminomethane.

12. The method of claim 11, wherein the hydrating step is accomplished by applying the salt solution to the wound dressing prior to the placing step.

13. The method of claim 11, wherein the hydrating step is accomplished by applying the salt solution to the first surface of the membrane prior to the covering step.

14. The method of claim 11, wherein the system further comprises a non-porous base layer and an edge of each of the transparent layer, the membrane layer, and the base layer are joined together.

15. The method of claim 14, wherein the indicator layer is integral with the transparent layer and does not extend to the edge of the transparent layer.

16. A method for detecting biological fluid on biomedical instruments and waste materials, the method comprising:

obtaining a system of claim 1 that includes a transparent layer, an indicator layer, and a membrane layer having a first surface and a second surface opposed to the first surface, the indicator layer being located between the transparent layer and the second surface, obtaining a biomedical instrument or waste material that has been in contact with a biological fluid, covering the biomedical instrument or waste material with the membrane layer such that the first surface of the membrane layer is in contact with the biomedical instrument or waste material, contacting the indicator layer with the second surface of the membrane layer, incubating the biomedical instrument or waste material with the system such that the biological fluid transfers through the membrane layer to the indicator layer and reacts with the colorimetric or fluorescent indicator reagent, and visualizing one or more color changes in the indicator layer through the transparent layer, wherein the one or more color changes in the indicator layer are each present at a location that came into contact with a component of the biological fluid present on the biomedical instrument or waste material and reacted with the colorimetric or fluorescent indicator reagent.

17. The method of claim 16, wherein the system further comprises a non-porous base layer and an edge of each of the transparent layer, the membrane layer, and the base layer are joined together.

* * * * *